Figure 1:
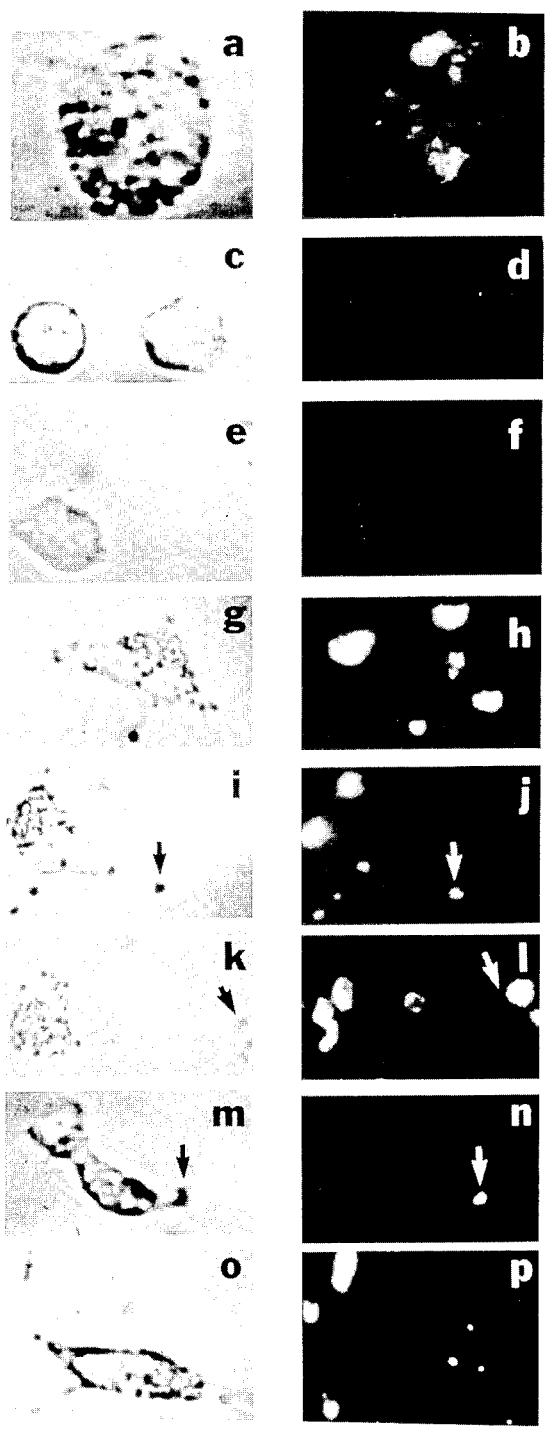

United States Patent [19]

Petty

[11] Patent Number: 4,830,961
[45] Date of Patent: May 16, 1989

[54] METHOD AND TEST KIT FOR ANALYSIS OF HISTAMINE RECEPTOR SITES OF MAMMALIAN CELLS

[75] Inventor: Howard R. Petty, Livonia, Mich.

[73] Assignee: Board of Governors of Wayne State University, Detroit, Mich.

[21] Appl. No.: 871,098

[22] Filed: Jun. 5, 1986

[51] Int. Cl.$^4$ .......................................... G01N 33/533
[52] U.S. Cl. ........................................ 435/34; 435/39; 436/503; 436/501; 436/546; 436/800; 436/805
[58] Field of Search ................... 435/34, 39, 810, 501; 436/503, 546, 800, 805, 808

[56] References Cited

U.S. PATENT DOCUMENTS

| | | | |
|---|---|---|---|
| 4,213,904 | 7/1980 | Haugland | 549/224 |
| 4,300,310 | 11/1981 | Galbraith | 47/58 |
| 4,433,051 | 2/1984 | Gilad | 436/546 |
| 4,435,509 | 3/1984 | Berthold et al. | 436/518 |
| 4,474,876 | 10/1984 | Osband et al. | 435/4 |
| 4,544,629 | 10/1985 | Rice et al. | 435/7 |

OTHER PUBLICATIONS

Dandliker, Cancer Research 38, pp. 4212–4224, (1978).
Muirhead et al., Journal of Immunology 135, 4120–4128 (1985).
Wulf et al., Proceedings of Natl. Academy of Science 76, 4498–4502, (1979).
Petty, H. R. et al., Biophys. J., 47, 837–840, (1985).
Zigmond, S. H. et al., J. Cell. Biol., 75, 606–616, (1977).
Keller, H. U. et al., Exp. Cell. Res. 122, 351–362, (1979).
Ferrante, A. et al., J. Immunol. Meth., 36, 109–117, (1980).
Petty et al., Proc. Natl. Acad. Sci. 77, 6587–6591, (1980).
Willingham et al., Cell 13, 501–507, (1978).
Osband et al., Blood 58, 87–90, (1981).
Beer, D. J. et al., Adv. Immunol. 35, 209–268, (1984).
Oliver, J. et al., Sem. Hematol. 20, 282–304, (1983).

*Primary Examiner*—Robert J. Warden
*Assistant Examiner*—Robert Benson
*Attorney, Agent, or Firm*—Ian C. McLeod

[57] ABSTRACT

A method and test kit for selectively staining histamine or histamine blocker sites on mammalian cells is described. Novel fluorescently labeled histamines or histamine blocker compounds are described. The method allows the visualization of sites on individual cells which are receptors for the histamines or histamine blockers.

2 Claims, 1 Drawing Sheet

METHOD AND TEST KIT FOR ANALYSIS OF HISTAMINE RECEPTOR SITES OF MAMMALIAN CELLS

BACKGROUND OF THE INVENTION (1) Summary of the Invention

The present invention relates to a method and test kit for analyzing histamine receptor sites of mammalian cells using novel fluorescent histamine or histamine blocker compounds which bind to the sites. In particular, the present invention relates to the use of 9-phenylxanthene fluorescent labeled histamine compounds for the analysis.

(2) Prior Art

The principal prior art is described in U.S. Pat. No. 4,474,876 to Osband et al. This patent describes the binding of multiple histamine or histamine blockers to a protein or peptide molecule with fluorescent compounds bonded to the protein or peptide for analytical purposes. The problems is that this fluorescent molecule does not bind to the sites of the cells or cell fragments in a way which allows histamine binding sites of the cells to be distinguished. A paper published by Muirhead et al in the Journal of Immunology 135, 4120 to 4128 (1985) suggests that this method is not effective to label only histamine active sites of the cells.

Wulf et al in Proceedings of National Academy of Science 76 (4498-4502) 1979 describe the fluorescent labeling of phallotoxin. U.S. Pat. No. 4,300,310 to Galbraith describes fluorescent labeling of heterokaryons. U.S. Pat. No. 4,435,509 to Berthold et al describes fluorescein isothiocyanate labeling which is enhanced by hypochlorite. None of this prior art shows site selective fluorescent labeling of cells.

OBJECTS

It is therefore an object of the present invention to provide an improved method and test kit for staining mammalian cells or cell fragments thereof using novel directly fluorescently labeled histamine or histamine blocker compounds. Further it is an object of the present invention to provide a staining method which is inexpensive and reliable. These and other objects will become increasingly apparent by reference to the following specification and the Figures.

IN THE FIGURES

FIG. 1 shows binding of the preferred F-His compound of the present invention to adherent human polyphosphonuclear leucocytes (PMNs) in Hank's balanced salt solution. Samples were treated as described in the specification with F-His at $10^{-5}$M followed by three washes with a buffer solution. Bright-field (a, c, e, g, i, k, and m) and fluorescence (b, d, f, h, j, l, and n) images were recorded. These photomicrographs show (a, b) stationary PMN; (c, d) PMN with excess histamine; (e, f) PMN with cimetidine; (g, h) PMN during chemokinesis; (i, j) PMN spontaneously polarized; (k, l) PMN polarized during chemotaxis and fixed with 2% paraformaldehyde; (m,n) PMN polarized during chemotaxis without fixation; (o,p) PMN polarized with f-met-leu-phe in the presence of ethylene diamine tetramine (EDTA) to inhibit locomotion. The areas of the uropods are indicated with arrows. (a,b×2,400; c-p×1,200).

GENERAL DESCRIPTION

The present invention relates to an improved method for analyzing mammalian cells to determine the receptors for histamine by preparing cells or cell fragments for staining and then staining the cells with a fluorescent labeled histamine or histamine blocker, which comprises staining the cells with a compound of the formula:

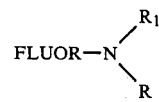

wherein FLUOR is a fluorescent group directly bonded to the

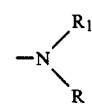

group and wherein

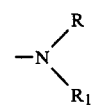

is selected from histaminic and histamine blocker groups which bond to histamine sites on the cells to thereby fluorescently stain the cells selectively at the histamine receptors.

The present invention also relates to a kit for assaying histamine receptors on cells which comprises a compound of the formula

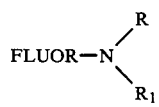

wherein FLUOR is a fluorescent group directly bonded to the

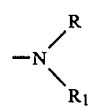

group and wherein

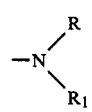

is a histamine or histamine blocker group and wherein the compound selectively binds to histamine receptors of mammalian cells wherein the compound is in a prepackaged form for the assaying.

The present invention further relates to a preferred compound of the formula:

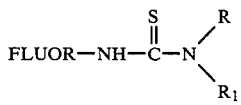

wherein FLUOR is a fluorescent group bonded to the NH group and wherein

is a histamine group or histamine blocker group and wherein the compound binds to histamine sites of mammalian cells.

The fluorescent compounds which can be attached to the histamine or histamine blocker molecule are well known to those skilled in the art. Fluorescent molecules with an isothiocyanate group are preferred since they easily react with the amino group on the histamine or histamine blocker compound. The useful fluorescent compounds include eosin, erythrosin, rodamine, Texas red, nitrobenzoxadiazole, coumain, acridine, stilbene, pyrene and anthacene compounds. These compounds generally have fused rings and various linking groups which react with amino groups, including isothiocyanate, succinimidyl, sulfonyl halide (iodo, or chloro), and acid groups. All of these fluorescent molecules are described in the Handbook of Fluorescent Probes and Research Chemicals, and available from Molecular Probes, Junction City, Oreg. and are well known to those skilled in the art.

The xanthene dye derived compounds as the fluorescent compounds are preferred, particularly the 9-phenylxanthenes. The most preferred compounds are fluorescein 5-isothiocyanates because of the superior results obtained in the method of the present invention.

The preferred FLUOR-Histamine compounds have the formula:

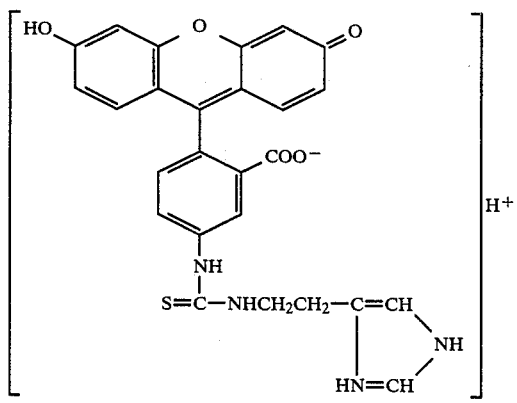

and metal salts thereof. U.S. Pat. No. 4,474,876 identifies many related histamine blocker or agonist compounds which can be labeled with the fluorescent compounds. These include 2(2-pyridyl)ethylamine, dimaprit, substituted histamines including 4-methylhistamine, diphenhydramine and cimetidine.

SPECIFIC DESCRIPTION

In this experimental effort, a univalent and bioactive fluorescent derivative of histamine was bound to the surface of human polymorphonuclear (PMN) leukocytes. Free histamine was found to compete with this derivative for binding sites. Histamine H2 receptor specificity was indicated by binding inhibition experiments using cimetidine (H2-specific) but not diphenhydramine (H1-specific). Video intensification fluorescence microscopy was used to determine the distribution of histamine receptors in living PMNs. Receptors appear as randomly distributed clusters upon stationary cells. During random locomotion, receptors were restricted to the ends of pseudopods while chemotaxis leads to receptor localization at lamellipodia and uropods. Ligand-receptor complexes were restricted to the cell surface as shown by quenching exterior fluorescence with crystal violet. Therefore pinocytic uptake cannot account for the observed receptor localization or clustering. As a further control, the lipid analog DiI remained uniformly distributed during all conditions. Histamine-mediated inhibition of adherence may be related to formation of ligand-receptor membrane domains at adherence sites.

Histamine is a well-known vasoactive amine that is released during the inflammatory component of acute allergic responses. Several laboratories have variously reported that histamine modulates polymorphonuclear (PMN) leukocyte chemokinesis, chemotaxis, degranulation, oxidative metabolism, and adherence. The broad spectrum of physiological reactions mediated by histamine are triggered by cell surface receptors. However, the cell surface topography of histamine receptors and their modulation during distinct cellular activities are not known. Furthermore, there was no suitable ligand available to obtain this information.

A univalent and bioactive fluorescent derivative of histamine that binds with high specificity to the surface of living human PMNs was synthesized. In addition to providing fresh information regarding cell surface properties of histamine receptors with a new fluorescence tool, the studies have suggested a possible structure-function correlation since the histamine-fluorescein conjugate (F-His), which inhibits adherence, accumulates at sites generally associated with adherence activity.

MATERIALS AND METHODS

Preparation of F-His

To prepare F-His, the side-chain nitrogen was converted to a secondary amine using fluorescein isothiocyanate (FITC) in ethanoloic NaOH. 14 mg of histamine and 10 mg of FITC were dissolved in 1:1 (vol./vol.) ethanol:0.1M NaOH and allowed to react in a light-tight test tube for 48 hours at 4° C. Histamine and FITC alone were treated in the same fashion as controls. Samples were acidified followed by thin-layer chromatography using 3:1:1 of chloroform, methanol, and ethanol as developing solvent. Analysis of the chromatograms revealed Rf values of 0.45, 0.55, and 0.81 for histamine, F-His, and FITC, respectively.

Preparation of Cells

PMNs were obtained from clot preparations as described (Petty, H. R., et al., Biophys. J. 47, 837–840 (1985); Zigmond, S. H. J. Cell Biol. 75, 606–616 (1977)).

This preparatory method was chosen because it minimizes perturbation of cell function caused by handling and purification procedures Drops of fresh blood were placed on glass coverslips in a humidified atmosphere at 37° C. for 30 minutes followed by gentle rinsing with saline to remove the clot. These preparations contained 92 to 95% neutrophils, ≦3% eosinophils, and 4–8% monocytes. Adherent PMNs were employed for further experimentation.

Cell Adhesion

Cell adhesion was measured by the method of Keller et al (Keller, H. U., et al., Exp. Cell. Res. 122, 351–362 (1979)). Neutrophils were isolated from human peripheral blood according to the method of Ferrante & Thong (Ferrante, A., and Y. H. Thong, J. Immunol. Meth. 36, 109–117 (1980)). The Ficoll-Hypaque solution was obtained from Packard Inst. Co. (Downers Grove, Ill. Neutrophils at $10^6$/ml in Hank's balanced salt solution (HBSS; Gibco, Grand Island, N.Y.) were incubated in tissue culture chamber/slides for 15 or 30 min. at 37° C. The slides were thoroughly washed, fixed with ethanol, then stained with Giemsa. Cell counts per unit area were made in the central region of the slide. Cells were untreated or treated with histamine or F-His. Adherence is given as % inhibition in comparison to matched controls.

Chemotaxis

Chemotaxis chambers were constructed as described by Zigmond (Zigmond, S. H., J. Cell Biol. 75, 606–616 (1977)).

N-formylmethionylleucylphenylalanine at 1 $\mu$M in HBSS+2% heat-inactivated fetal calf serum was used. In some cases coverslips were removed from the chamber followed by fixation with 2% paraformaldehyde in saline for 3 to 5 minutes. Samples were then labeled as described below. For studies with living cells, receptors were labeled as described below followed by insertion into the Zigmond chamber. In all cases the chamber was kept at a nominal temperature of 37° C. using an Incu-stage incubator (Lab-Line Inst., Melrose Park, Ill.).

Cell Labeling

Cells were labeled with F-His or 1,1'-dioctadecyl-3,3,3'3'-tetramethylindicarbocyanine (diI) on coverslips. F-His at 25 $\mu$M in 4:6 ethanol:H$_2$O was diluted in PBS to various final concentrations prior to application to coverslips. In typical experiments 10 $\mu$M F-His was used to label cells for 5 minutes at 4° C. The reagent diI was obtained from Molecular Probes, Inc. (Junction City, Oreg.). For diI labeling 10 $\mu$l of a 300 $\mu$M solution in ethanol was diluted into 1 ml of PBS. Labeling was performed for 5 minutes at room temperature. Samples were washed three times with PBS.

Fluorescence Microscopy

Cells were examined in a Zeiss fluorescence microscope equipped with special excitation and detection instrumentation. The device is a combination of fluorescence recovery after photobleaching and video-intensified microscopy (Petty, H. R., et al., Proc. Natl. Acad. Sci. 77 6587–6591; Willingham, M. C., et al. Cell 13, 501–507 (1978)). An argon-ion laser (model 164-09; Spectra-Physics Inc., Mountain View, Calif.) operating at 488 nm or 514 nm was used for excitation of F-His or diI, respectively. The intensity was adjusted by plasma tube current density, neutral density filters, and a beamsplitter assembly (Petty, H. R., et al., Proc. Natl. Acad. Sci. 77, 6587–6591 (1980)). The beam was spatially filtered, expanded (Earling Corp. South Natick, Mass.), and reflected into the epi-fluorescence port. A light level was chosen which did not photobleach the sample. Leitz 50× (n.a.=1.0) or 100× (n.a.=1.2) water immersion objective were employed. In these experiments, the image was reflected onto an RCA silicon-intensifier tube held in a Dage-MTI model 65 camera. Video signals were recorded on a Panasoni NV-8050-high resolution video recorder and displayed on an Audiotronics monitor. The photographs reported were taken from the screen using a Polaroid camera.

RESULTS

The bioactivity of F-His was tested using a previously described adherence assay (Keller, H. U., et al., Exp. Cell. Res. 122, 351–362 (1979)). These experiments showed 55±7% adherence of PMNs to glass coverslips in comparison to controls in a 15 min. assay at $10^{-5}$ M histamine and F-His, respectively.

After exposure of PMNs to F-His at 4° C. for 15 minutes at $10^{-5}$ M, fluorescence was distributed in clusters (FIGS. 1a and b). Maximal binding of F-His to PMNs was found at $10^{-5}$ M. This is in good agreement with the results of Osband et al (Osband, M. E., et al., Blood 58, 87–90 (1981)) using radiolabeled histamine. The clusters were predominantly associated with the cell surface as judged by moving the focal plane through the cell (for additional controls, see below). The clusters cannot be due to extracellular crosslinkage since F-His is univalent. Binding was specific since inclusion of a 100-fold excess of histamine abrogated binding (FIGS. 1c and d). In addition, this controls for bulk-phase pinocytic uptake (but not receptor-mediated uptake; see below) of F-His and non-specific membrane permeation. Both of these phenomena were undetectable. We have also tested the effects of the H2 antagonist cimetidine on F-His binding to PMNs. In FIGS. 1e and f we show the PMNs labeled with $10^{-5}$M F-His in the presence of 1 mM cimetidine; no labeling can be observed. The H1 antagonist diphenhydramine has no observable effect upon F-His binding at 1 mM (data not shown). These results are in agreement with previous reports (Beer, D. J., et al. Adv. Immunol 35, 209–268 (1984)) indicating the H2 specificity of the PN histamine receptor.

Cell locomotion and polarization result in profound alterations in the distribution of histamine receptors at the PMN surface. In FIGS. 1g and h we show a PMN undergoing chemokinesis in the presence of F-His. Ligand-receptor complexes were found at the ends of pseudopods and microvilli. Fluorescence cannot be found in association with the cell body. Under these conditions some PMNs spontaneously polarize (FIGS. 1i and j). In this case, receptors were associated with the leading edge and uropod. Polarization and chemotaxis were induced by gradients of f-met-leu-phe (Zigmond, S. H., J. Cell Biol. 75, 606–616 (1977)). Fluorescence was associated with the lamellipodium and/or uropod (FIGS. 1k and l) after fixation with 2% paraformaldehyde for 3 to 5 minutes. In the absence of fixation, receptors are rapidly redistributed to the uropod (FIGS. 1m and n). In the presence of EDTA, PMN locomotion but not polarization is inhibited. Again, fluorescence was found at the lamellipodium and/or uropod (FIGS. 1o and p). Small membranous vesicles arising from retraction fibers at the uropod were also labeled (FIG. 1p).

DISCUSSION

The results of the present invention are of technological and biological significance. F-His represents the first fluorescent histamine receptor probe which retains biological activity and receptor and pharmacological specificity. These conditions have generally not been fulfilled by previous histamine receptor probes using protein carries (Ganellin, C. R., et al., Pharmacology of Histamine Receptors. Wright PSG, London (1982); Beer, D. J., et al., Adv. Immunol 35, 209–268 (1984)).

The physiological role of the histamine ligand-receptor clusters is immediately suggested by their location. Puctate fluorescence is observed upon stationary cells. Cell locomotion leads to redistribution of fluorescence to pseudopods or to the lamellipodium and uropod. These cellular sites are responsible for adherence of PMNs and fibroblasts to substrates. Therefore, accumulation of histamine ligand-receptor complexes at these sites may sterically exclude membrane components participating in adhesion or decrease adhesion through the action of a second messenger such as cAMP. In either case a structure-function correlation is suggested. Accumulation of histamine receptors at the leading edge of migrating PMN may also increase cell sensitivity to an extracellular mediator such as histamine. Previous studies have indicated that certain cell surface components undergo topographic reorganizations during cell movement, endocytosis, or capping (Oliver, J. M., et al. Sem. Hematol. 20, 282–304 (1983)). The results of the present study are consistent with the Oliver-Berlin wave model of receptor redistribution (Oliver, J. M., et al. Sem. Hematol. 20, 282–304 (1983)). Moreover, the results clearly indicate that cross-linkage of receptors by multivalent ligands is not a requirement for cell surface responses fitting the Oliver-Berlin model, although receptor-receptor cross-linkage is not ruled out. The fluorescence label described above is applicable to the study of histamine receptors in their many diverse physiological settings using microscopic and flow cytometric techniques. The development of H1- and H2-specific fluorescent labels should allow for simultaneous localization of these distinct receptors.

The present invention can be used for:

(1) The fluorescence detection and assay of histamine receptors using flow cytometry, fluorescence microscopy, and fluorescence spectroscopy.

(2) The characterization of peripheral blood leukocytes including:
  (A) analysis of normal and diseased leukocytes.
  (B) analysis of leukemic cells.
  (C) analysis of immunoenhancement mediated by H2 antagonists.
  (D) Enumeration of histamine receptor bearing cells.

(3) Fluorescent 1-methyl and 4-methyl histame derivatives which measure H1 and H2 specific cells.

(4) Determination of H1 and H2 mediated neurotransmission pathways.

(5) Measurement of serum histamine levels with a reverse competition assay.

(6) The fluorescent histamine label can be used to identify and subsequently remove histamine receptor positive lymphocytes in immunosuppressive disorders (e.g., AIDS). Histamine suppresses the immune response.

(7) In addition to the immunological and neurological applications suggested above, histamine receptors are associated with:
  gastric secretion,
  vascular system,
  smooth muscle (alimentary, genitourinary, etc.)
  heart,
  lung and thus can be analyzed with the method of the present invention. Many additional applications for the fluorescent labeled histamines of histamine blockers will occur to those skilled in the art.

It is intended that the foregoing description be only illustrative of the present invention and that the present invention be limited only by the hereinafter appended claims.

I claim:

1. In a method for analyzing mammalian cells including living cells to determine the receptors for histamine by preparing cells or cell fragments for staining and then staining the cells or cell fragments, the improvement which comprises staining the cells with a compound of the formula:

$$\text{Fluor}-NH-\overset{\overset{S}{\|}}{C}-NH-CH_2CH_2-C=CH\diagdown_{NH}\diagup_{N=CH}$$

wherein FLUOR is a fluorescent 9-phenylxanthane moiety with the 9-phenyl group bonded to the NH group.

2. The method of claim 1 wherein the compound has the formula $$\left[\begin{array}{c}\text{structure with HO, O, =O, COO}^-, \text{NH, S=C-NHCH}_2\text{CH}_2\text{-C=CH, NH, HN=CH}\end{array}\right] H^+$$

and metal salts thereof.

* * * * *

UNITED STATES PATENT AND TRADEMARK OFFICE
CERTIFICATE OF CORRECTION

PATENT NO. : 4,830,961
DATED : May 16, 1989
INVENTOR(S) : Howard R. Petty

It is certified that error appears in the above-identified patent and that said Letters Patent is hereby corrected as shown below:

Column 1, line 22, "problems" should be --problem--.

Column 5, line 3, a period --.-- should be inserted after "procedures".

Column 6, line 11 "Panasoni" should be --Panasonic--.

Column 6, line 47 "PN" should be --PMN--.

Column 7, line 58 "histame" should be --histamine--.

UNITED STATES PATENT AND TRADEMARK OFFICE
CERTIFICATE OF CORRECTION

PATENT NO. : 4,830,961
DATED : May 16, 1989
INVENTOR(S) : Howard R. Petty

It is certified that error appears in the above-identified patent and that said Letters Patent is hereby corrected as shown below:

Column 8, structure of Claim 2 should read as follows:

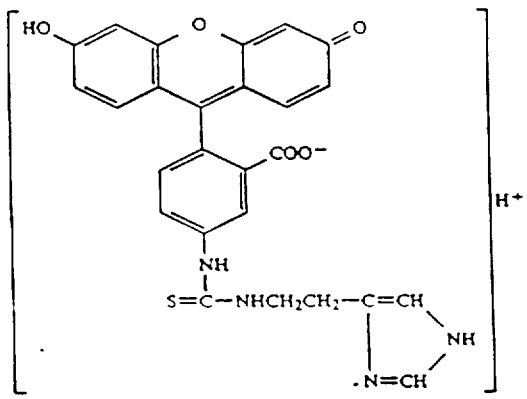

Signed and Sealed this

Nineteenth Day of June, 1990

*Attest:*

*Attesting Officer*

HARRY F. MANBECK, JR.

*Commissioner of Patents and Trademarks*